US009234226B2

(12) United States Patent
Barnes

(10) Patent No.: US 9,234,226 B2
(45) Date of Patent: Jan. 12, 2016

(54) IN VITRO RECOMBINATION METHODS USING 5' EXONUCLEASE

(76) Inventor: Wayne M. Barnes, University City, MO (US)

( * ) Notice: Subject to any disclaimer, the term of this patent is extended or adjusted under 35 U.S.C. 154(b) by 721 days.

(21) Appl. No.: 13/124,369

(22) PCT Filed: Oct. 14, 2009

(86) PCT No.: PCT/US2009/060640
§ 371 (c)(1),
(2), (4) Date: Aug. 19, 2011

(87) PCT Pub. No.: WO2010/045326
PCT Pub. Date: Apr. 22, 2010

(65) Prior Publication Data
US 2011/0300583 A1 Dec. 8, 2011

Related U.S. Application Data

(62) Division of application No. 61/196,060, filed on Oct. 14, 2008.

(51) Int. Cl.
C12P 19/34 (2006.01)

(52) U.S. Cl.
CPC .................................... C12P 19/34 (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 5,616,494 A | 4/1997 | Barnes | |
| 6,033,851 A | 3/2000 | Yamane | |
| 6,403,341 B1 | 6/2002 | Barnes et al. | |
| 6,673,576 B1 | 1/2004 | Usuda et al. | |
| 6,709,825 B2 | 3/2004 | Mirkin et al. | |
| 7,776,532 B2 * | 8/2010 | Gibson et al. | 435/6.12 |
| 2004/0203016 A1 | 10/2004 | Elledge et al. | |
| 2005/0136447 A1 | 6/2005 | Elledge et al. | |
| 2007/0037196 A1 | 2/2007 | Gibson et al. | |
| 2007/0037197 A1 | 2/2007 | Young et al. | |
| 2007/0292954 A1 * | 12/2007 | Elledge | 435/488 |
| 2009/0215648 A1 | 8/2009 | Elledge et al. | |
| 2009/0275086 A1 | 11/2009 | Gibson et al. | |
| 2010/0035768 A1 | 2/2010 | Gibson et al. | |
| 2010/0184187 A1 | 7/2010 | Young et al. | |
| 2012/0053087 A1 | 3/2012 | Gibson et al. | |

FOREIGN PATENT DOCUMENTS

WO    WO 2010045362    4/2010

OTHER PUBLICATIONS

Yang et al. (Nucleic Acids Research, 1993, 21(8):1889-1893).*
Li et al. (Nature Methods, 2007, 4(3):251-256).*
Tillett et al. (NAR, 1999, 27(19):e26, p. i-iii).*
Arditti et al., The Nature of Mutants in the lac Promoter Region, Lett. Ed. In J. Mol. Biol., 1968, pp. 421-426, vol. 38.
Aslanidis et al., Ligation-independent cloning of PCR products (LIC-PCR), Nucleic Acids Research, 1990, pp. 6069-6074, vol. 18, No. 20.
Barnes et al., Magnesium precipitate hot start method for PCR, Molecular and Cellular Probes, 2002, pp. 167-171, vol. 16.
Barnes, PCR amplification of up to 35-kb DNA with high fidelity and high yield from lambda bacteriophage templates, Proc. Natl. Acad. Sci. USA, 1994, pp. 2216-2220, vol. 91.
Baskaran et al., Uniform Amplification of a Mixture of Deoxyribonucleic Acids with Varying GC Content, Genome Research, 1996, pp. 633-638, vol. 6.
Bevis et al., Rapidly maturing variants of the Discosoma red fluorescent protein (DsRed). Nature Biotechnology, 2002, pp. 83-87, vol. 20.
Datsenko et al., One-step inactivation of chromosomal genes in Escherichia coli K-12 using PCR products, Proc. Natl. Acad. Sci. USA., 2000, pp. 6640-6645, vol. 97, No. 12.
Dickson et al., Genetic Regulation: The Lac Control Region, Science, 1975, pp. 27-35, vol. 187.
Dickson et al., Nucleotide Sequence Changes Produced by Mutations in the lac Promoter of Escherichia coli, J. Mol. Biol., 1977, pp. 65-75, vol. 111.
Dower et al., High efficiency transformation of E. coli by high voltage electroporation, Nucleic Acids Research, 1988, pp. 6127-6145, vol. 16, No. 13.
Ghadessy et al., Directed evolution of polymerase function by compartmentalized self-replication, Proc Natl Acad Sci USA, 2001, pp. 4552-4557, vol. 98, No. 8.
Gibson et al., Complete Chemical Synthesis, Assembly, and Cloning of a Mycoplasma genitalium Genome, Science, 2008, pp. 1215-1220, vol. 319.
Hamilton et al., Duplex strand joining reactions catalyzed by vaccinia virus DNA polymerase, Nucleic Acids Research, 2007, pp. 143-151, vol. 35, No. 1.
Hartley et al., DNA Cloning Using In Vitro Site-Specific Recombination, Genome Research, 2000, pp. 1788-1795, vol. 10.
Hsiao, Exonuclease III induced ligase-free directional subcloning of PCR products, Nucleic Acids Research, 1993, pp. 5528-5529, vol. 21, No. 23.

(Continued)

Primary Examiner — Stephanie K Mummert
(74) Attorney, Agent, or Firm — Dentons US LLP

(57) ABSTRACT

Provided herein is a method for homologous end cloning using a 5'-exonuclease. One aspect provides a method of generating a recombinant DNA molecule comprising 5' exonuclease digestion of DNA molecules, exonuclease inactivation, annealing of 3' overhangs to form a annealed complex. Also provided is a method a method of generating a recombinant DNA molecule comprising 5' exonuclease digestion of DNA molecules, exonuclease inactivation, annealing of 3' overhangs to form a annealed complex, and extension of 3' ends to fill gaps corresponding to exonuclease removal to form a substantially non-gapped annealed complex. Also provided is a one reaction method in which no further additions need be made to the reaction mixture and the reaction mixture is only manipulated thereafter as to incubation time and incubation temperature. Complexes formed according to methods described herein can be transformed into a host cell without further in vitro processing.

39 Claims, 7 Drawing Sheets

(56) References Cited

OTHER PUBLICATIONS

International Search Report and Written Opinion dated Dec. 24, 2009 in related PCT Application No. PCT/US2009/060640 filed Oct. 14, 2009, 8 pages.

Kerr et al., The Involvement of Genes 3, 4, 5 and 6 in Genetic Recombination in Bacteriophage T7, Virology, 1975, pp. 281-285, vol. 65.

Lee et al., In vitro recombination of bacteriophage T7 DNA detected by a direct physical assay, J. Virology, 1983, pp. 647-653, vol. 48, No. 3.

Li et al., Harnessing homologous recombination in vitro to generate recombinant DNA via SLIC, Nature Methods, 2007, pp. 251-256, vol. 4, No. 3.

Link et al., Beyond toothpicks: new methods for isolating mutant bacteria, Nature Reviews, 2007, pp. 680-688, vol. 5, No. 9.

Liu et al., The univector plasmid-fusion system, a method for rapid construction of recombinant DNA without restriction enzymes, Curr. Biol., 1998, pp. 1300-1309, vol. 8, No. 24.

Sadowski et al., Genetic recombination of bacteriophage T7 DNA in vitro, Proc. Natl.Acad. Sci. USA, 1976, pp. 692-696, vol. 73, No. 3.

Sagner et al., Rapid filter assay for the detection of DNA polymerase activity: direct identification of the gene for the DNA polymerase from Thermus aquaticus, Gene, 1991, pp. 119-123, vol. 97, No. 1.

Sanger et al., Nucleotide sequence of bacteriophage phi XI 74 DNA, Nature, 1977, pp. 687-695, vol. 265.

Studier et al., Use of T7 RNA Polymerase to Direct Expression of Cloned Genes, Methods in Enzymology, 1990, pp. 60-89, vol. 185.

Studier, Protein production by auto-induction in high-density shaking cultures, Protein Expr Purif., 2005, pp. 207-234, vol. 41, No. 1.

Subramanian et al., The enzymatic basis of processivity in lambda exonuclease, Nucleic Acids Res., 2003, pp. 1585-1596, vol. 31, No. 6.

Thomas et al., Processivity of DNA Exonucleases, J. Biol. Chem., 1978, pp. 424-429, vol. 253, No. 2.

Tillett et al., Enzyme-free cloning: a rapid method to clone PCR products independent of vector restriction enzyme sites, Nucleic Acids Research, 1999, pp. e26 (i-iii), vol. 27, No. 19.

Walhout et al., GATEWAY recombinational cloning: application to the cloning of large numbers of open reading frames or ORFeomes, Methods in Enzymology, 2000, pp. 575-592, vol. 328.

Weiner et al., Site-directed mutagenesis of double-stranded DNA by the polymerase chain reaction, Gene, 1994, pp. 119-123, vol. 151.

Yang et al., Construction of recombinant DNA by exonuclease recession, Nucleic Acids Research, 1993, pp. 1889-1893, vol. 21, No. 8.

Yu et al., T7 Single Strand DNA Binding Protein but Not T7 Helicase Is Required for DNA Double Strand Break Repair, Journal of Bacteriology, 2001, pp. 1862-1869, vol. 183, No. 6.

Zhu et al., In-Fusion assembly: seamless engineering of multidomain fusion proteins, modular vectors, and mutations, BioTechniques, 2007, pp. 354-359, vol. 43, No. 3.

\* cited by examiner

```
                        26mer primer T7 gen 10 rC                                    primer T8.81 for 15 bp overlap
                                                                          24mer primer T8.80  ----->       DsRed codons
    5290        5300        5310        5320        5330        5340        5350        5360
AAATAATTTGTTTAACTTTAAGAAGGAGATATACATGCACCACCATCATCACCATCATGCCAGTCCGAGGACGTGATA
                                   MetHisHisHisHisHisHisAlaSerSerGluAspValIle
                                   <-------------------------
                                   Vector primer V8.79 complements here.
```

FIG. 2

SEQUENCE LISTING

<160> NUMBER OF SEQ ID NOS: 13

<210> SEQ ID NO 1
<211> LENGTH: 31
<212> TYPE: DNA
<213> ORGANISM: Artificial Sequence
<220> FEATURE:
<223> OTHER INFORMATION: primer V8.79rC
<220> FEATURE:
<221> NAME/KEY: misc_feature
<222> LOCATION: (31)..(31)
<223> OTHER INFORMATION: ribobase

<400> SEQUENCE: 1
atgatggtga tgatggtggt gcatgtatat c        31

<210> SEQ ID NO 2
<211> LENGTH: 24
<212> TYPE: DNA
<213> ORGANISM: Artificial Sequence
<220> FEATURE:
<223> OTHER INFORMATION: primer T8.80rU
<220> FEATURE:
<221> NAME/KEY: misc_feature
<222> LOCATION: (24)..(24)
<223> OTHER INFORMATION: ribobase

<400> SEQUENCE: 2
atgcaccacc atcatcacca tcau        24

<210> SEQ ID NO 3
<211> LENGTH: 30
<212> TYPE: DNA
<213> ORGANISM: Artificial Sequence
<220> FEATURE:
<223> OTHER INFORMATION: primer T8.81

<400> SEQUENCE: 3
catcatcacc atcatgccag ctccgaggac        30

<210> SEQ ID NO 4
<211> LENGTH: 30
<212> TYPE: DNA
<213> ORGANISM: Artificial Sequence
<220> FEATURE:
<223> OTHER INFORMATION: primer 8.92

<400> SEQUENCE: 4
ggaagggaag aaagctagct tacaggaaga        30

<210> SEQ ID NO 5
<211> LENGTH: 26
<212> TYPE: DNA
<213> ORGANISM: Artificial Sequence
<220> FEATURE:
<223> OTHER INFORMATION: primer V41
<220> FEATURE:
<221> NAME/KEY: misc_feature
<222> LOCATION: (26)..(26)
<223> OTHER INFORMATION: ribobase

<400> SEQUENCE: 5
gctttcttcc cttcctttct cgccac        26

<210> SEQ ID NO 6
<211> LENGTH: 26
<212> TYPE: DNA
<213> ORGANISM: Artificial Sequence
<220> FEATURE:
<223> OTHER INFORMATION: primer T41
<220> FEATURE:
<221> NAME/KEY: misc_feature
<222> LOCATION: (26)..(26)
<223> OTHER INFORMATION: ribobase

<400> SEQUENCE: 6
gtggcgagaa aggaagggaa gaaagc        26

<210> SEQ ID NO 7
<211> LENGTH: 52
<212> TYPE: DNA
<213> ORGANISM: Artificial Sequence

```
<220> FEATURE:
<223> OTHER INFORMATION: primer V41_pET11d bandaid

<400> SEQUENCE: 7
ttcgggcttt gttagcagcc ggatccgtgg cgagaaagga agggaagaaa gc         52

<210> SEQ ID NO 8
<211> LENGTH: 43
<212> TYPE: DNA
<213> ORGANISM: Artificial Sequence
<220> FEATURE:
<223> OTHER INFORMATION: primer 82.20

<400> SEQUENCE: 8
ctatatccgg ctcgaggagc aatggcgatg acgcatcctc acg                   43

<210> SEQ ID NO 9
<211> LENGTH: 43
<212> TYPE: DNA
<213> ORGANISM: Artificial Sequence
<220> FEATURE:
<223> OTHER INFORMATION: primer 82.21

<400> SEQUENCE: 9
gccattgctc ctcgagccgg atatagttcc tcctttcagc aaa                   43

<210> SEQ ID NO 10
<211> LENGTH: 41
<212> TYPE: DNA
<213> ORGANISM: Artificial Sequence
<220> FEATURE:
<223> OTHER INFORMATION: primer 8.55

<400> SEQUENCE: 10
cgggcagtga gaattcgggg aaatgtgcgc ggaaccccta t                     41

<210> SEQ ID NO 11
<211> LENGTH: 41
<212> TYPE: DNA
<213> ORGANISM: Artificial Sequence
<220> FEATURE:
<223> OTHER INFORMATION: primer 8.54

<400> SEQUENCE: 11
acatttcccc gaattctcac tgcccgcttt ccagtcggga a                     41

<210> SEQ ID NO 12
<211> LENGTH: 48
<212> TYPE: DNA
<213> ORGANISM: Artificial Sequence
<220> FEATURE:
<223> OTHER INFORMATION: primer 82.44

<400> SEQUENCE: 12
tttaagaagg agatatacat ggccagctcc gaggacgtga taaaagag              48

<210> SEQ ID NO 13
<211> LENGTH: 26
<212> TYPE: DNA
<213> ORGANISM: Artificial Sequence
<220> FEATURE:
<223> OTHER INFORMATION: primer T7gen10rC
<220> FEATURE:
<221> NAME/KEY: misc_feature
```

```
<222> LOCATION: (26)..(26)
<223> OTHER INFORMATION: ribobase

<400> SEQUENCE: 13
gtttaacttt aagaaggaga tatatc                                                26
```

IN VITRO RECOMBINATION METHODS USING 5' EXONUCLEASE

CROSS-REFERENCE TO RELATED APPLICATIONS

This application claims the benefit of PCT International Application No.
PCT/US09/606040, filed Oct. 14, 2009; which claims priority from U.S. Provisional Application Serial No. 61/196,060 filed on Oct. 14, 2008, all of which are incorporated herein by reference in their entireties.

INCORPORATION-BY-REFERENCE OF SEQUENCE LISTING

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present invention generally relates to methods of cloning recombinant DNA. More specifically, the present invention relates to a method of ligase independent cloning.

BACKGROUND OF THE INVENTION

Methods for cloning recombinant DNA began with restriction enzymes and ligase to join vector replicon such as a plasmid with target passenger DNA to be cloned. PCR allows the ready generation of the target and/or vector DNA fragments with short overlapping sequence homology at their ends, enabling so-called ligase independent cloning (LIC). These methods obviate to lesser or greater extents that any particular sequence or recognition site be present at the ends of the DNA regions to be joined. An early LIC method required a certain sequence simplicity at the ends to be joined (only 3 bases complexity(1)) and single-strand ends were produced by the plus method (2) which involves treatment with 1 dNTP and the 3'-exonuclease of a DNA polymerase.

Other LIC methods make use of specially prepared, special vectors with special site-specific sites (3-5) or 2 sizes of both vector and target, followed by complete denaturation and reannealing (6).

Ribocloning (7) requires special PCR primers for both target and vector that end in a ribo-U or a ribo-C at their 3'-ends, treatment by RNAse in low salt, and removal of the released primers for maximum efficiency.

Some LIC methods use an overlap of normal DNA nucleotides, but employ digestion on the 3'-end by any of several exonucleases, such as ExoIII (8), T4 DNA polymerase (9-11), or vaccinia virus DNA polymerase (12), creating 5'-sticky end single strands.

It was reported in one of the T4 DNA polymerase methods (10) that the 5'-exonucleases encoded by phage T7 and lambda are less effective and reproducible.

SUMMARY OF THE INVENTION

Among the various aspects of the present invention is the provision of a method for homologous end cloning using a 5'-exonuclease. Various methods described herein exhibit advantages over other ligase-independent cloning methods, such as sequence independence, simplicity, robustness and efficiency. No abnormal primers, abnormal nucleotides, 5'-phosphate, ligase, blunted end, nor restriction enzyme, nor any particular vector are necessary, but all are compatible. Various methods described herein allow use of a single reaction mixture, which after formation is modulated only with respect to incubation time and temperature. A product of various methods described can be transformed into a host cell without further in vitro processing.

One aspect of the invention provides a method of generating a recombinant DNA molecule. In some embodiments, the method includes contacting a 5' exonuclease and at least two DNA molecules under conditions sufficient to create a 3' overhang on the DNA molecules. The DNA molecules generally include at least a first DNA molecule and a second DNA, where the DNA molecules comprise first linear double stranded DNA molecule and a second linear double stranded DNA molecule, respectively. The DNA molecules (e.g., the first DNA molecule and the second DNA molecule) are substantially homologous at terminal ends for at least about 15 up to about 50 bases. The reaction conditions for contacting the 5' exonuclease and the DNA molecules include a first incubation temperature and for a first incubation time.

In some embodiments, the method includes inactivating the 5' exonuclease under conditions sufficient to inactivate the 5' exonuclease without substantially denaturing the at least two DNA molecules. The reaction conditions for inactivating the 5' exonuclease include a second incubation temperature for a second incubation time.

In some embodiments, the method includes annealing homologous ends of the DNA molecules (e.g., the first DNA molecule and the second DNA molecule) under conditions sufficient to form an annealed complex. The annealing reaction conditions include a third incubation temperature and a third incubation time.

In some embodiments, the annealed complex is capable of transformation into a host cell without further in vitro processing.

In some embodiments, the method includes contacting an annealed complex, at least one polymerase, and a plurality of dNTPs under conditions sufficient to allow extension of a 3' end of a DNA molecule (e.g., the first DNA molecule or the second DNA molecule) of the annealed complex. Such extension fills a gap corresponding to exonuclease removal, for example a slight excess of exonuclease removal, thereby forming a substantially non-gapped annealed complex. In some configurations, the reaction conditions for gap filling are those of the annealing reaction.

In some embodiments, the substantially non-gapped annealed complex is capable of transformation into a host cell without further in vitro processing.

In some embodiments, the first incubation temperature is about 0° C. In some embodiments, the first incubation time is about 5 minutes to about 15 minutes. In some configurations, the first incubation time is about 15 minutes.

In some embodiments, the second incubation temperature is about 75° C. In some embodiments, the second incubation time is about 15 minutes.

In some embodiments, the third incubation temperature is about 44° C. to about 55° C. In some configurations, the third incubation temperature is about 52° C. In some embodiments, the third incubation time is about 10 minutes.

In some embodiments, the first DNA molecule is a target DNA molecule. In some embodiments, the second DNA molecule is a linearized vector In some embodiments, the first DNA molecule is a target DNA molecule and the second DNA molecule is a linearized vector. In some embodiments, the vector is a bacterial vector, a viral vector, a yeast vector, a plant vector, or an animal cell vector.

In some embodiments, the non-gapped annealed complex is a linear non-gapped annealed complex. In some embodiments, the non-gapped annealed complex is a circular non-gapped annealed complex.

In some embodiments, the first DNA molecule and the second DNA molecule are substantially homologous at terminal ends for at least about 15 up to about 50 bases. In some configurations, the first DNA molecule and the second DNA molecule are substantially homologous at terminal ends for at least about 18 up to about 40 bases. In some configurations, the first DNA molecule and the second DNA molecule are substantially homologous at terminal ends for at least about 22 up to about 33 bases. In some configurations, the first DNA molecule and the second DNA molecule are substantially homologous at terminal ends for at least about 24 up to about 36 bases.

In some embodiments, the annealed complex comprises about 3 to about 5 linked DNA molecules.

In some embodiments, the 5' exonuclease is a T7 exonuclease. In some configurations, the T7 exonuclease is present at about 0.7 units per 20 µl reaction volume.

In some embodiments, the exonuclease reaction mixture (for contacting the 5' exonuclease and the at least two DNA molecules) includes about 1 to about 10 mM DTT. In some configurations, the exonuclease reaction mixture includes about 10 mM of DTT. In some configurations, the exonuclease reaction mixture includes about 10 mM of freshly added DTT. In some configurations, the exonuclease reaction mixture includes about 100 µg/ml BSA.

In some embodiments, the at least one polymerase is Vent, Deep Vent, Pfu, Klentaq1, KlentaLA, TactLA, Taq, or KOD, or mixtures thereof. In some embodiments, especially those where the polymerase is present during exonuclease deactivation, the at least one polymerase is a thermostable polymerase. In some configurations, the at least one thermostable polymerase is a Taq polymerase or a Klentaq polymerase, or a mixture thereof. In some embodiments, the at least one thermostable polymerase is present at about 0.25 units per 20 µl reaction volume.

In some embodiments, gap filling includes contacting the annealed complex, a plurality of dNTPs, and a polymerase mixture. In some configurations, the polymerase mixture includes an Archeal polymerase and at least one polymerase or thermostable polymerase. In some configurations, the polymerase mixture includes an Archeal polymerase and one or more of a Taq polymerase and a Klentaq polymerase. In some embodiments, the polymerase mixture is present at about 0.25 units per 20 µl reaction volume.

In some embodiments, the method includes transforming or transfecting a host cell with the annealed complex. In some configurations, a host cell is transformed or transfected with the annealed complex directly from an annealing reaction mixture without further in vitro processing.

In some embodiments, the method includes transforming or transfecting a host cell with the substantially non-gapped annealed complex. In some configurations, a host cell is transformed or transfected with the substantially non-gapped annealed complex directly from an annealing and extending reaction mixture without further in vitro processing.

In some embodiments, the yield of transformants or transfectants is greater than about 100 transfected or transformed host cells per 10 ng of a first DNA molecule (e.g., a target DNA molecule). In some embodiments, the yield of transformants or transfectants is at least about 1,000 to about 3,000 clones per ng of a first DNA molecule (e.g., a target DNA molecule). In some embodiments, the host cell is an E. coli.

In some embodiments, the method includes amplifying a target DNA molecule (e.g., a first DNA molecule) in a polymerase chain reaction (PCR); and removing or de-activating substantially all primers used in the PCR of the first DNA molecule. In some configurations, the PCR comprises one or more polymerases selected from the group consisting of Vent, Deep Vent, Pfu, Klentaq1, KlentaLA, TactLA, Taq, or KOD, or mixtures thereof.

In some embodiments, a DNA molecule (e.g., a first DNA molecule, which can be a target DNA molecule) is at a concentration less than about 0.5 ng per ul of a reaction mixture. In some configurations, the DNA molecule is at a concentration less than about 0.4 ng per ul of a reaction mixture. In some configurations, the DNA molecule is at a concentration less than about 0.3 ng per ul of a reaction mixture.

In some embodiments, a first reaction mixture is formed to include a 5' exonuclease; a thermostable polymerase; a plurality of dNTPs (e.g., dATP, dTTP, dCTP, and dGTP); at least a first DNA molecule and a second DNA molecule. In some configurations, no further additions are made to the reaction mixture and the reaction mixture is only manipulated thereafter as to incubation time and incubation temperature. In some configurations, the substantially non-gapped annealed complex formed from the reaction mixture is capable of transformation into a host cell without further in vitro processing. In some configurations, the first incubation temperature is about 0° C.; the second incubation temperature is about 75° C.; and the third incubation temperature is about 44° C. to about 55° C. In some configurations, the first incubation time is about 5 minutes to about 15 minutes; the second incubation time is about 15 minutes; and the third incubation time is about 10 minutes. In some configurations, the reaction mixture further comprises DTT. In some configurations, the reaction mixture further comprises BSA.

In some embodiments, the method does not include use of one or more of a restriction enzyme; a restriction site sequence; a joining enzyme; a topoisomerase; or a recombinase. In some embodiments, the method does not include use of any of a restriction enzyme; a restriction site sequence; a joining enzyme; a topoisomerase; or a recombinase Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 1 is diagram illustrating an embodiment of the joining method described herein.

FIG. 2 is a schematic depiction of PCR primers and DNA sequence surrounding one of two vector/target joins for exemplary clonings in one embodiment of the method, which was used to create plasmid pWB536 several times. Underlined portion of numbered sequence is homology and numbering to vector pET11d (20). PCR primer sequences are as recited in Example 1. Three different extents of overlapping homology can be tested with the primers shown in FIG. 2. One end of the vector PCR was primed by primer V8.79. For 15 bp overlap, the target PCR was primed at one end by T8.81; for 24 bp overlap by T8.80; and for 49 bp overlap by T7gen10rC.

DETAILED DESCRIPTION OF PRESENTLY PREFERRED EMBODIMENTS

Provided herein is a method for homologous-end cloning using a 5'-exonuclease. The present invention is based, at least in part, on the discovery that use of a 5'-exonuclease offers the possibility of extension of the resulting 3'-sticky ends, and thus extension of the recombinant join, by a simultaneously-included DNA polymerase.

For DNA fragments with short mutual homologies at their ends, treatment with T7 exonuclease on ice, followed by heating to about 75° C. and then annealing, is an efficient way to recombine the DNA fragments in vitro. To tighten the recombinant join before transformation, and produce about 3 to about 10 times more recombinants, the sticky 3'-ends can be extended onto the recombinant partner DNA by the initial inclusion of dNTPs and a DNA polymerase (e.g., Taq). PCR-product vector and target can then be processed together in one tube, after it can be immediately ready for electroporation. Various embodiments of the method exhibit several advantages over other ligase-independent cloning (LIC) methods in terms of sequence independence, simplicity, robustness and efficiency. No abnormal primers, abnormal nucleotides, 5'-phosphate, ligase, blunted end, nor restriction enzyme, nor any particular vector are necessary, but all are compatible. The joining reaction can produces up to about 6,000 recombinants per ng of vector, depending on cell competence.

Embodiments of the method described herein, using a 5'-exonuclease, may be compared to recent methods which accomplish the same thing using a 3'-exonuclease activity of DNA polymerase to create 5'-sticky ends which may be productively annealed. Yang et al. (9) and Gibson et al. (11) halted the T4 DNA polymerase with heat denaturation (and then added back fresh enzyme after annealing), and Li & Elledge (10) halted the extent of exonuclease after 15 min. by the addition of one dNTP. The proprietary method In-Fusion has been reported (12) to similarly utilize the DNA polymerase of vaccinia virus, which has been reported to be self-limiting at about 15 bases for its 3'-exonuclease (24). In contrast, various embodiments of the method described herein conveniently halts the exonuclease by 75° C. treatment, and remains flexible in the extent of 5'-end removal merely by adjusting the initial incubation time at 0° C.

Previous methods (7,10) prepare the vector and target separately, and then mix them together for annealing. As presented here for maximum convenience, various embodiments of the method described herein mix unmodified vector and target together, and process them together in one tube. If desired, the vector and target can be treated separately with 5'-exonuclease through the exonuclease digestion step and the exonuclease inaction step, and then combined in a subsequent step for annealing and optional Taq DNA polymerase extension.

Figure 4:
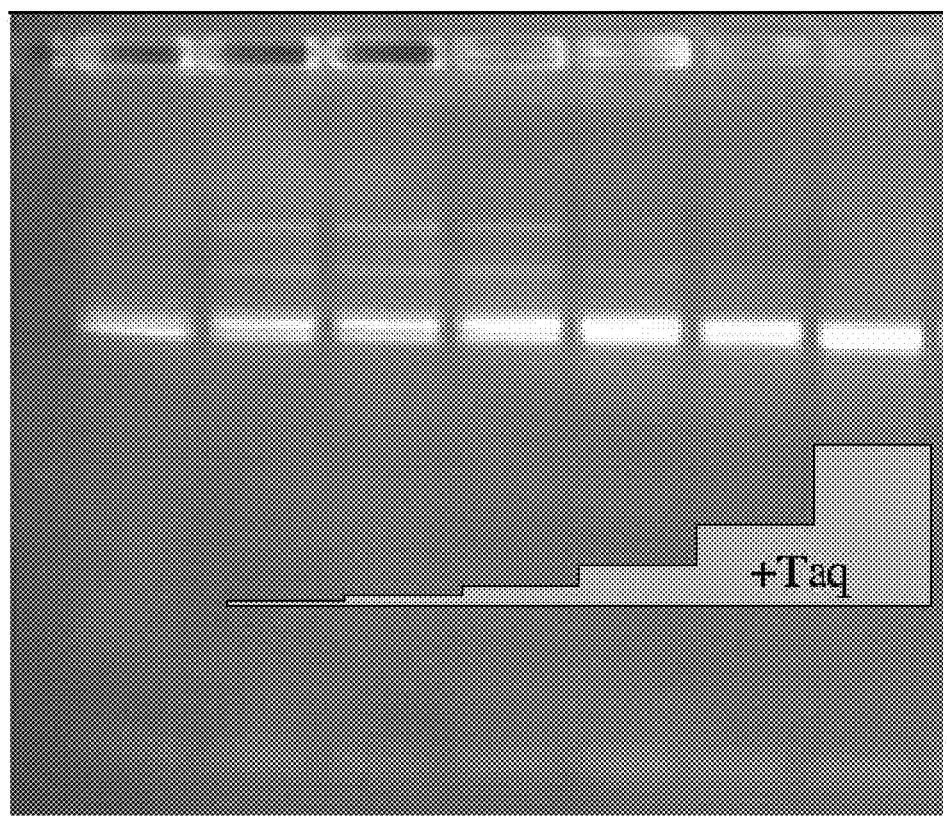
FIG. 4 is photographic image of a gel with an information overlay showing the level of Taq DNA polymerase added to the joining reaction as 2-fold serial dilutions from 5 units in the right-most column. No Taq was added to the experiment of the left-most lane. Unattached vector is labeled "V" and unattached target DNA is labeled "T". Slower moving bands are recombinant DNA products; the band labeled oc is open circle target+vector and other slow bands (not labeled) are vector+target, target+vector+target, and (perhaps) vector+target+vector.

As shown herein, up to 900,000 clones per reaction were obtained (see e.g., FIG. 4, 6000 clones per ng), which is 10 to 100 times more than any previous report. But such efficiency depends greatly on the level of electrocompetence, which is rarely reported. As such, it can be difficult to directly compare the DNA joining efficiency with other published methods. Electrocompetence of cells is reported herein (colonies per ug of purified, super-coiled plasmid) to facilitate comparison when more data in third party studies becomes available.

Various embodiments of the method described herein provide enzymatic and procedural elements analogous to all four T7-encoded enzymes necessary for recombination between T7 DNA molecules in vivo: exonuclease, DNA polymerase, endonuclease and ssb (25-28). Taking these in order, a T7 phage exonuclease can be used directly. For the DNA polymerase functionality, a Klentaq1 DNA polymerase shares sequence, crystal structure, and functional homologies (but not any 3'-exonuclease) with a T7 DNA polymerase. The 5'-exonuclease of full-length Taq DNA polymerase only removes up to 1 or 2 nucleotides from 5' ends, as evidenced by it leaving a triplet band on sequencing gels (29) so this slight 5'-activity is not significant to our joining method. It is thought that the T7 endonuclease requirement is satisfied by use of fragments of DNA that are already "cleaved". Finally, use of high temperature for the anneal/extend joining event provides for functionality of a single-stranded binding protein(25). As would ssb at 30° C., the high temperature of the annealing denatures single-strand structure and ensures high sequence specificity for the recombinant annealing.

Figure 1A:
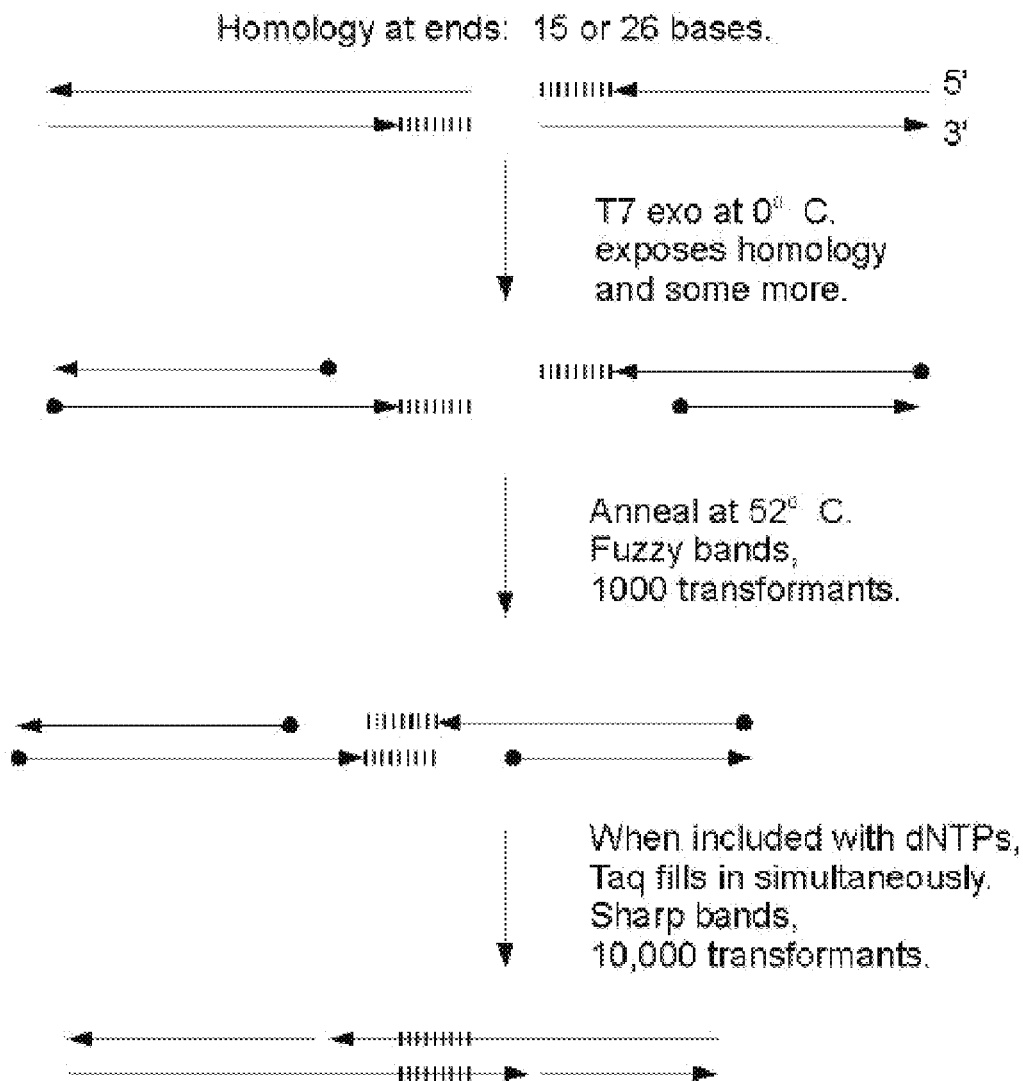
FIG. 1A is a schematic of DNA molecules being joined in one embodiment of the method.
Figure 1B:
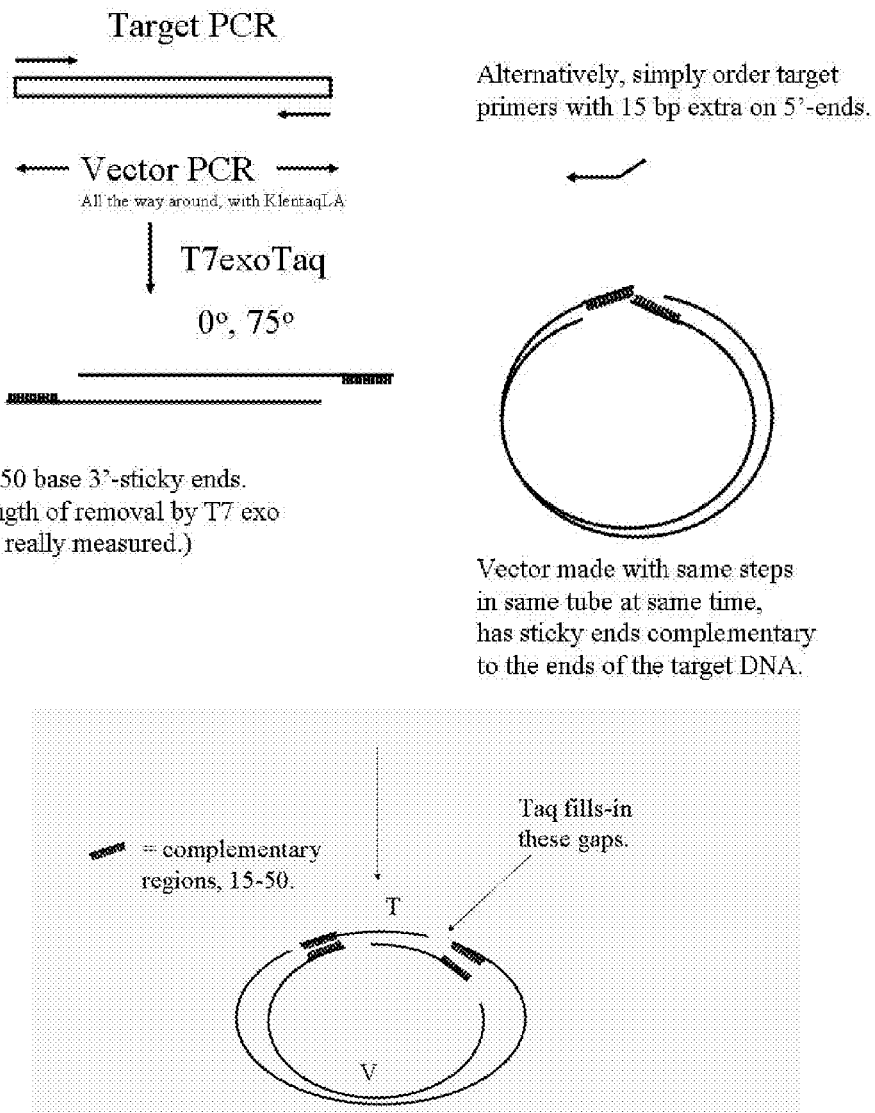
FIG. 1B is a schematic of a circular vector plasmid V and target DNA T being joined in one embodiment of the method.

The method of generating a recombinant DNA molecule can include an exonuclease digestion step, an exonuclease deactivating step, and an annealing step (see e.g., FIG. 1). Optionally, the method can include an extension step, wherein the non-gapped annealed complex is a linear non-gapped annealed complex. The annealed complex can be a circular annealed complex. The annealed complex can be a linear annealed complex. The annealed complex can be a substantially non-gapped annealed complex. The annealed complex can be a substantially non-gapped circular annealed complex. The annealed complex can be a substantially non-gapped linear annealed complex.

All components of the joining method can be combined in one reaction mixture. The reaction mixture can be reacted in 3 phases by modulating the incubation time and temperature. In some embodiments, where all components are combined into one reaction mixture, no further additions are made to the reaction mixture and the reaction mixture is only manipulated thereafter as to temperature.

In some embodiments, the joining method does not include use of one or more of a restriction enzyme; a restriction site sequence; a joining enzyme; a topoisomerase; or a recombinase. In some embodiments, the joining method does not include use of any of a restriction enzyme; a restriction site sequence; a joining enzyme; a topoisomerase; or a recombinase.

The product of the joining method, an annealed complex, can be transformed into a host cell without further in vitro processing.

DNA Fragments

Methods provided herein can join multiple DNA fragments (e.g., vector plasmid and target gene) having short mutual homologies at their ends. At least two, at least three, at least four, at least five, or more, DNA fragments can be so joined. For example at least about 3 to about 5 DNA molecules can be linked to form an annealed complex.

A first DNA fragment will usually comprise a target DNA sequence. The target DNA sequence can be any type of DNA sequence including, but not limited to, a natural occurring DNA sequence, a transgenic DNA sequence, or a synthetic DNA sequence.

In some embodiments, a first (target) DNA fragment can be at a concentration of less than about 0.5 ng per ul of a reaction mixture. For example, a first (target) DNA fragment can be at a concentration of less than about 0.5 ng per ul of a reaction mixture; less than about 0.4 ng per ul of a reaction mixture; or less than about 0.3 ng per ul of a reaction mixture.

A DNA fragment can be amplified (e.g., in a polymerase chain reaction (PCR)) prior to the joining method described herein. Preferably, all or substantially all DNA fragment specific primers are removed from a reaction mixture prior to the start of the joining method. In some embodiments, the joining method includes amplifying a DNA fragment in a PCR and removing or de-activating substantially all primers used in the PCR. An optional amplification PCR can include one or more polymerases, such as Vent, Deep Vent, Pfu, Klentaq1, KlentaLA, TactLA, Taq, or KOD, or mixtures thereof.

Another DNA fragment (e.g., a second DNA fragment) can be a vector. The vector can be any type of vector including, but not limited to, a bacterial vector, a viral vector, a yeast vector, a plant vector, and an animal cell vector. The vector can be a linearized vector or a circular vector.

While there are no particular limits to the length of this homology, less than 12 is expected to be less stable and less specific.

DNA fragments (e.g., a first target DNA molecule and a second vector DNA molecule) can be substantially homologous at terminal ends. Generally, fragments that are meant to be consecutive will have substantial homology at terminal ends. Where order is not important, all DNA fragments can share the same or similar substantial homology.

The DNA fragments can be substantially homologous for at least about 13 bases. While there are no particular limits to the length of this homology, less than 12 is expected to be less stable and less specific. DNA fragments can be substantially homologous for up to about 50 bases. For example, the DNA fragments can be substantially homologous for at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, or at least about 50. For example, the DNA fragments can be substantially homologous for at least about 15 base up to about 50 bases. As another example, the DNA fragments can be substantially homologous for at least about 18 base up to about 40 bases. As another example, the DNA fragments can be substantially homologous for at least about 22 up to about 33 bases. As another example, the DNA fragments can be substantially homologous for at least about 24 up to about 36 bases.

Exonuclease Digestion Step

The joining method described herein includes a 5' exonuclease digestion step. The reaction mixture containing the 5' exonuclease and DNA fragments is incubated under conditions sufficient to create a 3' overhang on the fragments. The exonuclease digestion reaction conditions include a first incubation temperature and a first incubation time.

The incubation temperature for exonuclease digestion can be at least about −5° C. Preferably, the incubation temperature for exonuclease digestion is about 0° C.

The incubation time for exonuclease digestion can be at least about 5 minutes. The incubation time for exonuclease digestion can be up to about 15 minutes. For example, the incubation time for exonuclease digestion can be at least about 5, at least about 6, at least about 7, at least about 8, at least about 9, at least about 10, at least about 11, at least about 12, at least about 13, at least about 14, or at least about 15 minutes. For example, the incubation time for exonuclease digestion can be at least about 5 minutes up to about 15 minutes. Preferably, the first incubation time is about 15 minutes.

The 5' exonuclease can be a T7 exonuclease. The Lambda exonuclease is less preferred for the desired limited action at all the DNA ends in a cloning reaction because it is highly processive (13,14). But T7 exonuclease is distributive and therefore more desirable for in vitro recombination, as it changes substrate molecules often during digestion(13), which is just what is wanted for a cloning method.

A T7 exonuclease can be present at least about 0.5 units per 20 µl reaction volume. A T7 exonuclease can be present up to about 1.0 units per 20 µl reaction volume. For example, T7 exonuclease can be present at least about 0.5 units up to about 1.0 units per 20 µl reaction. Preferably, a T7 exonuclease is present at about 0.7 units per 20 µl reaction volume.

The exonuclease digestion reaction mixture can contain DTT. The exonuclease digestion reaction mixture can contain at least about 1 nM DTT. The exonuclease digestion reaction mixture can contain up to about 10 mM DTT. For example, the exonuclease digestion reaction mixture can contain at least about 1 nM up to about 10 mM DTT. Preferably, the DTT is freshly added. Preferably, the DTT is substantially non-reacted, substantially non-volatized or substantially non-oxidized. In some embodiments, substantially non-reacted, non-volatized, or non-oxidized DTT is freshly added to the exonuclease digestion reaction mixture.

The exonuclease digestion reaction mixture can contain BSA. In some embodiments, the exonuclease digestion reaction mixture can contain about 100 µg/ml BSA.

Exonuclease Inactivation

The joining method described herein includes an exonuclease inactivation step. A reaction mixture including a 5' exonuclease is incubated under conditions sufficient to substantially deactivate the 5' exonuclease. Preferably, the exonuclease deactivation incubation conditions do not substantially denature the DNA fragments to be joined. The exonuclease inactivation reaction conditions include a second incubation temperature and a second incubation time.

The incubation temperature for exonuclease inactivation can be at least about 75° C. The incubation temperature for exonuclease inactivation can be up to about 80° C. For example, the incubation temperature for exonuclease inactivation can be about 75, about 76, about 77, about 78, about 79, or about 80° C. For example, the incubation temperature for exonuclease inactivation can be at least about 75° C. up to about 76° C. Preferably, the incubation temperature for exonuclease inactivation is about 75° C.

The incubation time for exonuclease inactivation can be at least about 5 minutes. The incubation time for exonuclease digestion can be up to about 20 minutes. For example, the incubation time for exonuclease digestion can be at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 minutes. For example, the incubation time for exonuclease inactivation can be at least about 5 minutes up to about 15 minutes. Preferably, the incubation time for exonuclease inactivation is about 15 minutes.

To avoid unwanted deletions, the exonuclease inactivation step (e.g., at 75° C.) should be thorough, and it might be preferable to use the 5-minute exonuclease conditions, since they should favor end-terminal and perfect homology over internal and partial homology. As shown herein, this 5 minute treatment time reduces the yield of recombinant colonies by about 2-4 fold, which is still ample for most purposes. If it is desired to enhance the frequency of deletions, longer T7 exonuclease times and a lower annealing temperature, such as 37° C. or 40° C., could be used.

Annealing

The joining method described herein includes an annealing step. A reaction mixture containing the DNA fragments having 3' overhangs is incubated under conditions sufficient to anneal homologous ends of the DNA fragments and to form an annealed complex. The annealing reaction conditions include a third incubation temperature and a third incubation time.

The incubation temperature for annealing can be at least about 44° C. The incubation temperature for annealing can be up to about 55° C. For example, the incubation temperature for annealing can be about 40, about 41, about 42, about 43, about 44, about 45, about 46, about 47, about 48, about 49, about 50, about 51, about 52, about 53, about 54, or about 55° C. For example, the incubation temperature for annealing can be at least about 44° C. up to about 55° C. Preferably, the incubation temperature for exonuclease inactivation is about 52° C.

The incubation time for annealing can be at least about 5 minutes. The incubation time for annealing can be up to about 20 minutes. For example, the incubation time for annealing can be at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 minutes. For example, the incubation time for annealing can be at least about 5 minutes up to about 15 minutes. Preferably, the incubation time for annealing is about 10 minutes.

Gap Filling

The joining method described herein can optionally include a gap filling step. A reaction mixture containing an annealed complex is incubated under conditions sufficient to fill a gap corresponding to exonuclease removal. The gap filling reaction mixture can include the annealed complex, at least one DNA polymerase, and a plurality of dNTPs (e.g., dATP, dTTP, dCTP, dGTP). In some embodiments, components of the gap filling reaction can be added at the beginning of the joining method. In some embodiments, components of the gap filling reaction can be added after the exonuclease deactivation step.

The gap filling reaction mixture can be incubated under conditions sufficient to allow extension of a 3' end of a DNA fragment of the annealed complex. Gap filling can occur under the same or similar conditions as the annealing step. In some embodiments, gap filling can occur during the annealing step. As such, gap filling incubation time and temperature can be those of the annealing incubation temperature and annealing incubation time.

In various embodiments, 3' ends of (e.g., target or vector 3' ends) an annealed complex are extended with a DNA polymerase. Such extension can fill a gap corresponding to exonuclease removal thereby forming a substantially non-gapped annealed complex. Such a substantially non-gapped annealed complex is capable of transformation into a host cell without further in vitro processing.

The use of Taq DNA polymerase can increase the effectiveness of the recombination by 3-5 fold (sometimes 10-fold, data not shown). While under no obligation to provide an underlying mechanism, and in no way limiting the present invention, it is presently thought that the extent of homology between DNA partners is increased by the DNA synthesis, the DNA join literally becomes tighter, and that the recombinant DNA is more likely to remain circular during shear stress of electroporation and/or repair by the bacterium. It is not clear, however, why recombinants at too-high levels of Taq DNA polymerase have decreased yield.

A DNA polymerase can be used in the gap filling step to extend 3' ends of (e.g., target or vector 3' ends) an annealed complex. Any DNA polymerase is suitable where it is added to the reaction mixture after an exonuclease deactivation (e.g., Vent, Deep Vent, Pfu, Klentaq1, KlentaLA, TactLA, Taq, or KOD, or mixtures thereof). Where the DNA polymerase is added prior to the exonuclease deactivation step, the DNA polymerase should be a thermostable DNA polymerase to survive the exonuclease deactivation incubation temperature. Preferred thermostable DNA polymerase include a Taq polymerase and a Klentaq polymerase, or a mixture thereof. Some embodiments can employ a polymerase mixture including an Archeal polymerase and one or more thermostable DNA polymerase. For example, the polymerase mixture can include an Archeal polymerase and one of more of a Taq polymerase and a Klentaq polymerase.

A DNA polymerase can present in the gap filling reaction mixture at least about 0.20 units per 20 µl reaction volume. A DNA polymerase can present in the gap filling reaction mixture at least about 0.20 units per 20 µl reaction volume. Preferably, a DNA polymerase can present in the gap filling reaction mixture at about 0.25 units per 20 µl reaction volume.

One Mix Reaction

All steps of the joining method can be performed in the same reaction mixture. In some embodiments, after formation of the reaction mixture, no further additions occur and the reaction mixture is manipulated thereafter as to incubation time and incubation temperature.

A reaction mixture can be formed from a 5' exonuclease; a thermostable polymerase; a plurality of dNTPs (e.g., dATP, dTTP, dCTP, or dGTP); and two or more DNA fragments to be joined. The substantially non-gapped annealed complex formed from the reaction mixture can be capable of transformation into a host cell without further in vitro processing.

In various one step embodiments, the reaction can include three incubation phases. The three incubation phases can be according to those described above. For example, the first incubation temperature can be about 0° C.; the second incubation temperature can be about 75° C.; and the third incubation temperature can be about 44° C. to about 55° C. As another example, the first incubation time can be about 5 minutes to about 15 minutes; the second incubation time can be about 15 minutes; and the third incubation time can be about 10 minutes. As above, the one step reaction mixture can include DTT or BSA).

Transformation

The joining method described herein can optionally include a transformation step. In some embodiments, a host cell is transformed or transfected with the annealed complex or the substantially non-gapped annealed complex. A host cell can transformed or transfected with the annealed complex or the substantially non-gapped annealed complex directly from an annealing (and optional extending) reaction mixture without further in vitro processing.

The host cell can be any suitable host cell (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). In some embodiments, the host cell is an *E. coli*.

As shown herein, up to 900,000 clones per reaction were obtained (see e.g., FIG. 4, 6000 clones per ng), which is 10 to 100 times more than any previous report. But such efficiency depends greatly on the level of electrocompetence, which is rarely reported. As such, it can be difficult to directly compare the DNA joining efficiency with other published methods. Electrocompetence of cells is reported herein (colonies per ug of purified, super-coiled plasmid) to facilitate comparison when more data in third party studies becomes available.

In some embodiments, the yield of transformants or transfectants can be greater than about 100 transfected or transformed host cells per 10 ng of a target DNA molecule.

The yield of transformants or transfectants can be at least about 1,000 clones per ng of a target DNA molecule. The yield of transformants or transfectants can be up to about 3,000 clones per ng of a target DNA molecule. For example, the yield of transformants or transfectants can be at least about 1,000 to about 3,000 clones per ng of a target DNA molecule.

Molecular Engineering

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art. Generally, conservative substitutions can be made at any position so long as the required activity is retained.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C.

in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m=81.5°$ C.$+16.6(\log_{10}[Na^+])+0.41$ (fraction G/C content)$-0.63$(% formamide)$-(600/l)$. Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Kits

Also provided are kits. Such kits can include the compositions of the present invention and, in certain embodiments, instructions for administration. Such kits can facilitate performance of the methods described herein. When supplied as a kit, the different components of the composition can be packaged in separate containers and admixed immediately before use. Components include, but are not limited to DNA fragments, a vector, one or more DNA polymerases, dNTPs, or a 5' exonuclease, each as described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the invention in detail, it will be apparent that modifications, variations, and equivalent embodiments are possible without departing the scope of the invention defined in the appended claims.

Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

The reaction buffer used was NEBuffer 4 from New England Biolabs (1×=50 mM potassium acetate, 20 mM Tris-acetate, 10 mM magnesium acetate, 1 mM Dithiothreitol (DTT), pH 7.9@25° C.) This buffer was routinely supplemented freshly (see 2×T7exoTaq mix, below) with DTT and BSA. This buffer was chosen in part because it is compatible with direct electroporation at up to 3-4 ul per 55 ul of electrocompetent E. coli cells. Equivalent results were obtained with a range of final concentrations of 1× to 2× of NEBuffer 4.

Vector PCR was catalyzed by KlentaqLA (15) using a magnesium precipitate hot start (16). The fairly narrow cycling parameters for successful vector amplification included 1 M betaine (17) and 22 cycles of 80 sec. 94°, 80 sec. 57°, 9 min. 60°. Usually, the target primers and the vector primers share 24-26 nucleotides of complementarity to each other. Sequence overlap is arranged by including a "bandaid" template oligonucleotide in the PCR reaction either for the targets or for the vector, as described by (7). Alternatively, for PCR of at least one member of the target/vector pair, PCR primers can simply be designed with 15-25 bases of the desired overlapping homology at the 5'-portion of the primers (8-10,12). We used this method for the target PCR for testing 15-16 bp overlaps.

Amplicon Purification

This 2-step method of amplicon purification may be substituted for by any common method. It is especially important to remove the PCR primers, since they compete directly at the cloning step.

(A) Dpn+Exo: After temperature cycling and agarose gel verification, 130 ul of PCR amplification reactions were supplemented with 2% by volume of a 1:1 mixture of DpnI and Exonuclease I (N.E. Biolabs, 20 units each) and incubated for 60-100 min. at 37° C., followed by 15 min. at 80°. The purpose of this optional incubation was to reduce the background of parental DNA by cleaving GATC-methylated template DNA (18), and to hydrolyze excess PCR primers.

(B) SDS+PEG: Except as otherwise provided, methods are according to (7). After DpnI+ExoI treatment, each PCR amplicon was treated with 1/20 volume (5-10 ul) of blue SDS [5% SDS, 1 mg/ml blue dextran], and ½ volume of sterile-filtered PEG+NaCl [30% PEG 3350, 1.5 M NaCl] and mixed thoroughly (Vortex). The amplicon DNA and blue dextran carrier/indicator was then pelleted by centrifugation at not more than 10 k rpm for 15-30 min. The 10 k rpm limit prevents rupture of the thin-walled 0.5 ml PCR tubes. The PEG pellet was recentrifuged with ca. 300 ul of 75% ethanol. A blue pellet was usually visible after this ethanol rinse. The blue pellet was air-dried briefly and resuspended in 50-200 ul of TEN and approximately quantified by agarose gel electrophoresis of 2 and 8 ul. Vector, target and standard DNA ladders were compared, in order to judge the approximate relative molarity of target and vector.

The order of steps (A) and (B) may be reversed. If so, it is recommended that NEB4 buffer be supplied for DpnI+ExoI as the second step, so that the DNA can then be added directly to the cloning reaction.

None of the recombination reactions described herein employed gel-purified DNA.

2×T7exoTaq mix: Mix was assembled with 110 ul water, 3 ul of 1 M DTT, 3 ul of BSA (10 mg/ml), 30 ul of 10× NEBuffer 4, 1 ul of T7 exonuclease (10 units; New England Biolabs), 0.75 ul of Taq DNA polymerase (NEB), and 3 ul of a stock mixture of all 4 dNTPs at 10 mM each.

Standard T7exoTaq cloning procedure: 100-200 ng of vector and 3-5× supramolar (i.e., 20-100 ng) target were combined in water or TEN, in 10 ul volume on ice. 10 ul of ice-cold 2×T7exoTaq mix (see above) were then added. Except where mentioned, incubations of 15', 10', and 10' for 0° C., 75° C. and 52° C. respectively, were applied to complete the reaction, and the steps after 0° C. were conveniently programmed into a thermal cycler. Completed reactions were held on ice for up to an hour and/or stored frozen at −20° C. Agarose gel analysis (1.4%) was routinely carried out for 12 ul of the annealed DNA, leaving 8 ul for up to several transformations, before or after freezer storage at −20° C.

For routine cloning without agarose gel analysis, 3 ul DNA, such as 1 ul vector and 2 ul target, was combined on ice with 3 ul 2×T7exoTaq mix to start the recombination.

Electrocompetent E. coli cells: Unless provided otherwise, preparation of cells were according to (19). After gentle, ice-cold water washes with ½, and 1/10 culture volumes, cells were gently resuspended in a minimal volume of cold 5% glycerol, 5% DMSO, and stored at −80 C. in aliquots of 120 ul. After thawing on ice, 55 ul of E. coli were electroporated at 1500 volts/1 mm with 3 ul of annealed cloning reaction, diluted immediately with 1 ml of LB broth, and allowed to recover for 1-2 hours at 30° or 37° C. before plating i.e. 200 ul. For highly competent cells (WB498), 2 ul of a 10-fold dilution was used to electroporate 30 ul of cells.

Strains and Plasmids

E. coli host strain was WB478. In brief, E. coli host strain was WB478 is BL21(20) modified to express a doubly-mutant T7 RNA polymerase (mutant T7 gene 1) between genes Z and Y of an otherwise wild-type lac operon. Similarly for WB498, modified from NEB strain C 3016.

A vector plasmid used as template was pWB535, which itself was prepared from pET11d by ribocloning using bandaid oligonucleotide template V41_pET11d and primer V41 to prime on the downstream side of the expressed gene, and primer VO1 to prime to the left, just upstream from the start codon. Subsequently (with pWB535 as template), the bandaid adapter oligo was not necessary for priming by V41. Irrelevantly, pWB535 carries, and can express, the colorless protein product of T7 gene 5.

Plasmid pWB536 consists of the above pET11 vector-PCR fragment recombined with a target fragment that encodes DsRed.T3 (21) from arbitrary codons assembled by the method of (22).

Construction of pWB584 employed the present T7exoTaq method, using a 5'-extension 16-bp overlap between 3-kb vector PCR product (primers 82.20 and 82.55 and modified pKD119 template) and 2-kb target PCR product (primers 82.21 and 8.54, pWB536 template). The result was to clone lacI through DsRed.T3 and T7 terminator portion of pWB536 into the pSC101-ts-replicon, using a modified (inverted-tetA, Barnes, unpublished) vector backbone from plasmid pKD119 (23).

Primers: Primers were supplied by IDT. Some primers have a 3'-ribo base, indicated by lower case c or u.

```
V8.79rC:
                                        (SEQ ID NO: 1)
ATG ATG GTG ATG ATG GTG GTG CAT GTA TATc.

T8.80rU:
                                        (SEQ ID NO: 2)
ATG CAC CAC CAT CAT CAC CAT CAu.

T8.81:
                                        (SEQ ID NO: 3)
CAT CAT CAC CAT CAT GCC AGC TCC GAG GAC.

8.92:
                                        (SEQ ID NO: 4)
GGA AGG GAA GAA AGC TAG CTT ACA GGA AGA.

V41:
                                        (SEQ ID NO: 5)
GCT TTC TTC CCT TCC TTT CTC GCC Ac.

T41:
                                        (SEQ ID NO: 6)
GTG GCG AGA AAG GAA GGG AAG AAA Gc.

V41_pET11d bandaid:
                                        (SEQ ID NO: 7)
TTC GGG CTT TGT TAG CAG CCG GAT CCG TGG
CGA GAA AGG AAG GGA AGA AAG C.

82.20:
                                        (SEQ ID NO: 8)
CTATATCCGG CTCGAG GAG CAA TGG CGA TGA
CGC ATCCTCACG.

82.21:
                                        (SEQ ID NO: 9)
GCCATTGCTCCTCGAGCCGGATATAG TTC CTC CTT
TCAGCAAA.

8.55:
                                        (SEQ ID NO: 10)
CGG GCA GTG AGA ATT CGG GGA AAT GTG CGC
GGA ACC CCTAT.

8.54:
                                        (SEQ ID NO: 11)
ACATTTCCCC GAATTC TCACTGCCCG CTTTCCAGTC
GGGAA.

82.44:
                                        (SEQ ID NO: 12)
TTT AAGAAGGAGA TATAC ATG GCC AGC TCC GAG
GAC GTG ATA AAA GAG.

T7gen10rC:
                                        (SEQ ID NO: 13)
GTT TAA CTT TAA GAA GGA GAT ATA Tc.
```

Example 2

Test Target and Vector

Methods are according to Example 1, unless provided otherwise.

An overview of the DNA end-joining method is provided in FIG. 1. The DNA fragments to be joined, such as vector plasmid and target gene, shared 15, 16, 24, 26, or 49 bases of homology at the ends to be joined.

All the ingredients were combined in one tube at one time, but the reaction was separated into 3 phases by incubation temperature. Phase 1 was 5-15 min. at 0° C. on ice, and T7 exonuclease removes an estimated 30-100 bases from each 5' end (actual number of removed bases not measured). Phase 2 was 5-15 min. at 75° C. to inactivate the T7 exonuclease. Phase 3 was 5-15 min. of annealing at decreased or decreasing temperature around 52° C. or 44° C. and allows the exposed, homologous 3'-ends to anneal to each other by complementary base pairing, and immediately extend onto the partner DNA, catalyzed by included Taq DNA polymerase. A portion of the 20 ul reaction (0.2 to 4 ul) may then used directly to transform competent bacteria.

Most of the test cloning experiments used a 709 or 729 bp target fragment containing 7 histidine codons at one end of an indicator gene coding for DsRed.T3 (21). Primers around the start of the indicator gene are shown in FIG. 2. For the 709 bp target, the PCR primer on this N-end (24 mer, T8.80rU) was actually the start codon ATG followed by the 7 histidine codons of a histidine tag. The other PCR primer T41 was complementary to the 26 bases just after the stop codon. The vector primers were the exact complements, except that the vector primer complementary to the histidine codons (primer 8.79) continued longer by 7 bases at its 3'-end. The template for the vector PCR was pWB535, which is nearly equivalent to pET11d (20) but without any cloning restriction site and carrying a gene for (colorless) his-tagged T7 DNA polymerase starting at its codon 8. The target size of 729 bp was defined by target and vector primers T7gen10rc and V01, which cover the Shine-Dalgarno ribosome binding sequence, shifted just to the left of the start codon.

Correct resulting recombinant plasmids expressed red color on plates containing lactose, but no color without lactose, or with added glucose instead of lactose. The latter lack of color was only confirmed occasionally, and is dependent on an intact lacI gene on the vector. When tested, red colonies did appear on glucose a frequency of about 0.2%, which is best explained as PCR-induced mutations in the vector plasmid's lac I gene. Based on the red phenotype, some 96% of the transformants were of the correct, non-mutant structure. Silent mutations were not detectable.

Although DpnI treatment was routinely used to suppress PCR template plasmids, an additional selection strategy was often used to be sure all red colonies were recombinants, not carry-over of target-template plasmid. A tetracycline-resistant plasmid was used as the source of the DsRed.T3 gene, by using pWB584 as template, and Ticarcillin to select recombinants.

Many of the vector and target primers for this study contained a terminal ribonucleotide, to enable a comparison and a backstop between this method and ribocloning. The resulting single ribonucleotide has no discernible or reported effect or impediment on the action of T7 exonuclease. Some demonstrated cloning has no ribo bases in the primers.

Example 3

Stability and Reliability of T7 Exonuclease

Methods are according to Examples 1-2, unless provided otherwise.

Initial experiments utilizing T7 exonuclease at 26° C. were only occasionally and slightly successful (data not shown), with extents of T7 exonuclease digestion varying from too little to too much, using 0.5 to 10 units of enzyme. Over- and under-digestion was apparent by attention to the 709 or 729 bp target band on agarose gels. This band was not visible when over-digested, and remained sharp when the T7 exonuclease had apparently not survived dilution. Few if any recombinant colonies resulted from over- or under-digestion. This reproducibility problem was suggested in a previous report (10) that found T7 exonuclease to be unreliable. The situation improved greatly when the buffer was supplemented with fresh DTT (1 mM, but see below for 10 mM) and with BSA and moved to 0° C. for the incubation temperature for T7 exonuclease.

Figure 3:
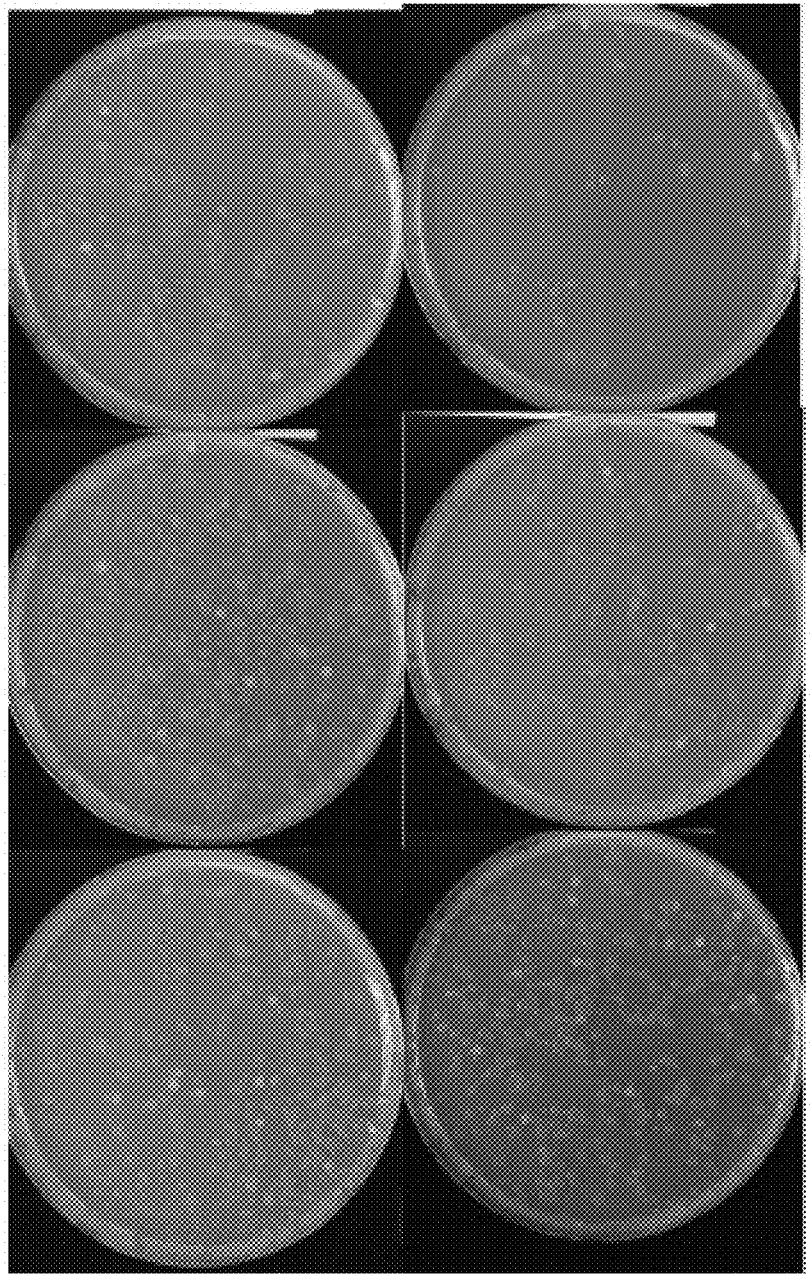
FIG. 3 is a series of photographs depicting recombinant colonies from an 10 mM DTT experiment. Top row: 10 mM DTT, decreasing T7 exonuclease left-to-right as in Table 1. Bottom row: 1 mM DTT. Sequence overlap was 24 bp on one side and 26 bp on the other. Vector PCR employed template pWB535, and primers V8.79rC and V41; target PCR employed pWB584 (tetR replicon), and primers T8.80rU and T41. Zero colonies were obtained for the control with no T7 exonuclease (photo not shown). After initial overnight incubation at 30° C., DsRed.T3 color was allowed to develop for 2 days at room temperature. Illumination is normal overhead laboratory visible light. Very small background colonies, if visible, are escapes from the Ticarcillin selection, arose later, and were not counted. Red and white transformants are enumerated in Table 1.

Under these conditions, the system is reproducible and reliable, and a serial dilution (more levels than shown in FIG. 3 and Table 1) showed that 0.7 units of T7 exonuclease (1 µL per 280-300 µL of reaction) was near optimum for a 20 µL reaction, as shown by retention of a fuzzy 1 kb target fragment band on agarose gel, and by production of many recombinants.

T7 exonuclease was optimally active over a broader range of dilutions when a full 10 mM of DTT was added, compared to 1 mM. This result is demonstrated by the experiment summarized in Table 1 and photographed in FIG. 3. Net cloning yield remained more constant over the range of T7 exonuclease added to each standard 20 µL reaction, varied at 1/14 µL, 1/28 µL and 1/56 µL. This table compares 10 mM and 1 mM DTT.

TABLE 1

10 mM DTT broadens optimum for T7 exonuclease level.

| | DTT | | | | | | |
|---|---|---|---|---|---|---|---|
| | <--------- 10 mM ------> | | | <------ 1 mM ---------> | | | 10 mM |
| 1/(T7 exo) ul$^{-1}$ | 14 | 28 | 56 | 14 | 28 | 56 | No exo |
| T7 exo units | 0.71 | 0.36 | 0.18 | 0.71 | 0.36 | 0.18 | 0 |
| Red colonies | 223 | 237 | 139 | 242 | 130 | 25 | 0 |
| Misclonings | 13 | 10 | 5 | 15 | 8 | 3 | 0 |

"Red colonies" denotes clones with the desired phenotype. "Misclonings" is a count of the other, non-red colonies (see FIG. 3); these were not further characterized, but they could be PCR errors, deletions, or empty vector. The fraction 1/35 of each reaction was plated, so the total maximum yield of correct recombinants in this experiment was 35×237~=8,000 per 150 ng of vector pET11. The transformation competency of the host cells was 1.5×10**7 per ug of pWB536 DNA.

Example 4

TAQ Titration

Because of using 3'-sticky ends, whether there was any advantage to extending the DNA join enzymatically by adding a DNA polymerase simultaneously was tested. A thermostable DNA polymerase was chosen for this purpose so that it would survive the 75° C. inactivation of the exonuclease, and so the extension could be immediate at high temperature, during the most sequence-specific phase of the annealing treatment.

Results showed there is an advantage to including *Thermus aquaticus* DNA polymerase ("Taq"), and there is an optimum level of Taq. The agarose gel in FIG. 4 demonstrates a range of levels of included Taq for the otherwise complete joining reaction, although only 1 mM fresh DTT was used in this experiment. Without the Taq, the recombinant bands are diffuse and often unrecognizable. When Taq is included, the recombinant circle band labeled "oc" usually sharpens significantly, unless too much Taq is used. Before sharpening, the broad recombinant bands can be explained as variable and excess 5'-removal by T7 exonuclease. As the excess single strands are filled in by extension of the 3'-homologous ends, the molecules become more uniform in structure, and this migrate together as a sharper band. Nearly identical results were obtained using Klentaq1 or KlentaLA. The latter enzyme preparations have no 5'-exonuclease, which is an indication that the 5'-endonuclease of Taq is not the activity that is involved.

Figure 5:
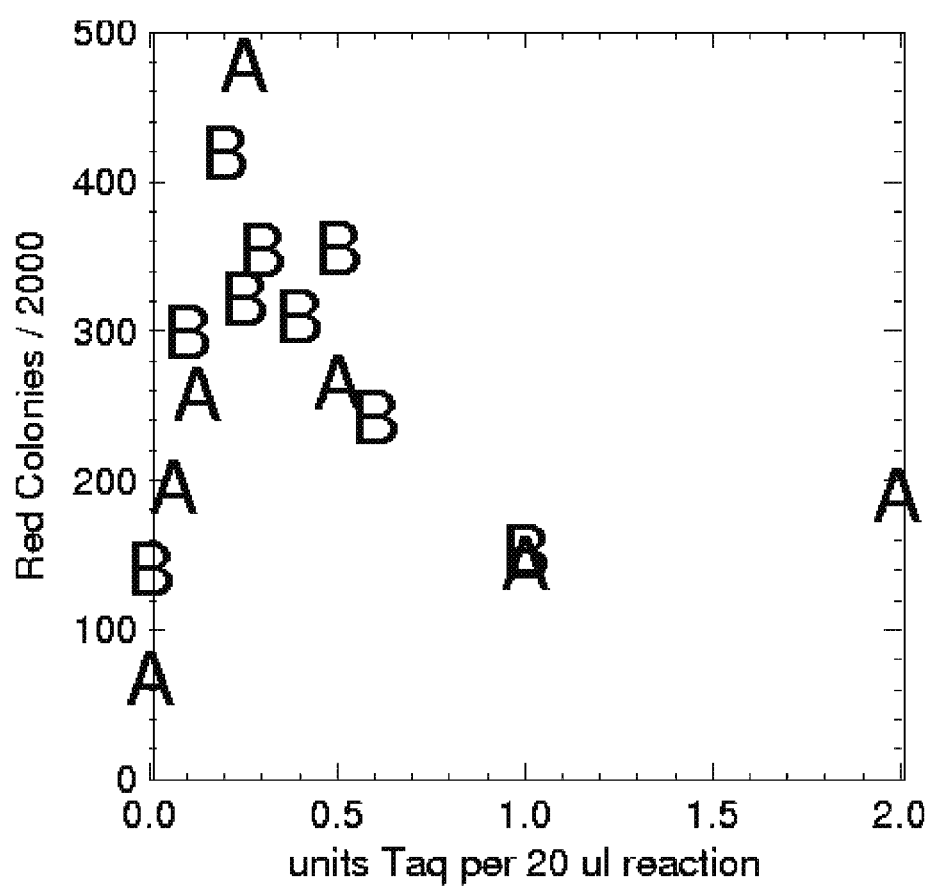
FIG. 5 is a scatter plot showing Red colonies as a function of titration of Taq (per 20 μL reaction) at 10 mM DTT and 0.7 units T7 exonuclease. The temperature incubation profile was 15 min, 15 min., 10 min. at 0° C., 75° C., and 52° C. respectively. Experiment A employed 2-fold dilutions of 2×T7exoTaq mix starting with 2 units/10 μL to achieve the various levels of Taq. Experiment B employed mixtures of 2× mix with and without 1 unit of Taq per 10 μL. 1/100 of each reaction was electoporated into 30 μL of WB498 cells, and 1/20 of these transformed WB498 cells were plated and scored for red colonies. White colonies were constant at about 3-4%. The average peak number of transformants was 478, corresponding to 900,000 for 150 ng of vector (supercoiled plasmid pWB536 competence for this batch of WB498 cells was 4×108 per μg). The average peak enhancement by Taq was 4.6-fold.

After the beneficial results above with 10 mM DTT, and to bracket the optimal level of Taq, a Taq titer was repeated several times at 10 mM DTT and 0.7 unit T7 exonuclease. Two representative experiments are shown in FIG. 5. This experiment employed *E. coli* cells (WB498) of high competence for electroporation, the maximum yield of recombinant plasmids per 150 ng of vector was 935,000, and the determined optimum level of Taq was around 0.25 unit per 20 ul reaction.

Example 5

Variations

Figure 6:
FIG. 6 is photographic image of a gel with an information overlay showing effect of variations on the incubation times and temperatures. This cloning employed terminal homologies of only 15 bp, 1 mM DTT, and Klentaq1 (0.1 unit/20 μL) instead of Taq. Cells of low competency (1×10**6/μg pWB536 DNA) were used here, so all the cells from a transformation with 3 μL of reaction were plated. Number of clone colonies is the count of correct (red) colonies on LB plates with added Ticarcillin and lactose. Misclonings percentage (data not shown) was similar to Table 2 (4-6%). Minutes "0*" is actually about 5-10 sec. Other "0" minutes refer to omission of the step. The condition labeled with "15+" 0° C. treatment actually experienced no overt inactivation of the T7 exonuclease, so it continued to digest for longer. The gel position of the goal recombinant molecule, open circle DNA, is indicated by "oc" in a lane where it was not visible. The 709 bp band is the target gene for DsRed.T3, was amplified with PCR primers 8.81 and 8.92, and overlaps the vector band by 15 bp of homology on either end. The vector (pET11) PCR product band has a size of 5689 bp and was amplified with PCR primers V8.79 and V41.

Several variations on the incubation steps were performed (see e.g., FIG. 6). Clones were obtained for all reasonable conditions tested. This experiment employed only 1 mM DTT and only 15 bp of overlap. Some productive T7 exonuclease digestion seems to occur during the few seconds of heating from 0° to 75° C., as shown by the "0 min. 0°" lane, which was, practically, 5-10" at 0°. A longer incubation, such as 10-15 min. at 0° C., increases the yield of recombinants about 10-fold, as shown.

A longer overlap of 49 bp on just one side was tested by using T7gen10rC-primed target and V8.89-primed vector (see FIG. 2; both other sides were T41/V41). Compared to a 26-bp overlap (V01-primed vector or T8.80-primed target), the yield of clones was about the same.

References

1. Aslanidis, C. and de Jong, P. J. (1990) Ligation-independent cloning of PCR products (LIC-PCR). *Nucleic Acids Research*, 18, 6069-6074.

2. Sanger, F., Air, G. M., Barrell, B. G., Brown, N. L., Coulson, A. R., Fiddes, J., Hutchison, C. A., Slocombe, P. M. and Smith, M. (1977) Nucleotide sequence of bacteriophage phi X174 DNA. *Nature*, 265, 687-695.
3. Hartley, J. L., Temple, G. F. and Brasch, M. A. (2000) DNA cloning using in vitro site-specific recombination. *Genome Research*, 10, 1788-1795.
4. Liu, Q., Li, M. Z., Liebham, D., Cortez, D. and Elledge, S. J. (1998) The univector plasmid fusion system, a method for rapid construction of recombinant DNA without restriction enzymes. *Curr. Biol.*, 8, 1300-1309.
5. Walhout, A. J., Temple, G. F., Brasch, M. A., Hartley, J. L., Lorson, M. A., van den Heuvel, S, and Vidal, M. (2000) GATEWAY recombinational cloning: application to the cloning of large numbers of open reading frames or ORFeomes. *Methods in Enzymology*, 328, 575-592.
6. Tillett, D. and Neilan, B. A. (1999) Enzyme-free cloning: a rapid method to clone PCR products independent of vector restriction enzyme sites. *Nucleic Acids Research*, 27, e26.
7. Barnes, W. M. 2003. Ribocloning: DNA cloning and gene construction using PCR primers terminated with a ribonucleotide, p. 441-449. In C. W. Dieffenbach and G S Dveksler, G. S. (Eds.), PCR Primer, 2d. edition. Cold Spring Harbor Press, NY.
8. Hsiao, K. (1993) Exonuclease III induced ligase-free directional subcloning of PCR products. *Nucleic Acids Research*, 21, 5528-5529.
9. Yang, Y.-S., J. Watson, W., W. Tucker, P. and Capra, J. D. (1993) Construction of recombinant DNA by exonuclease recession. *Nucleic Acids Research*, 21, 1889-1893.
10. Li, M. Z. and Elledge, S. J. (2007) Harnessing homologous recombination in vitro to generate recombinant DNA via SLIC. *Nature Methods*, 4, 251-256.
11. Gibson, D., Benders, G., Andrews-Pfannkoch, C., Denisova, E., Baden-Tillson, H., Zaveri, J., Stockwell, T., Brownley, A., Thomas, D. and Algire, M. (2008) Complete Chemical Synthesis, Assembly, and Cloning of a *Mycoplasma genitalium* Genome. *Science*, 319, 1215.
12. Zhu, B., Cai, G., Hall, E. O. and Freeman, G. J. (2007) In-Fusion™ assembly: seamless engineering of multidomain fusion proteins, modular vectors, and mutations. *BioTechniques*, 43, 354-359.
13. Thomas, K. R. and Olivera, B. M. (1978) Processivity of DNA exonucleases. *J. Biol. Chem.*, 253, 424-429.
14. Subramanian, K., Rutvisuttinunt, W., Scott, W. and Myers, R. S. (2003) The enzymatic basis of processivity in lambda exonuclease. *Nucleic Acids Res.*, 31, 1585-1596.
15. Barnes, W. M. (1994) PCR amplification of up to 35 kb DNA with high fidelity and high yield from lambda bacteriophage templates. *Proc. Natl. Acad. Sci.*, 92, 2216-2220.
16. Barnes, W. M. and Rowlyk, K. R. (2002) Magnesium Precipitate Hot Start Method for PCR. *Molecular and Cellular Probes*, 16, 167-171.
17. Baskaran, N., Kandpal, R., Bhargava, A., Glynn, M., Bale, A. and Weissman, S. (1996) Uniform amplification of a mixture of deoxyribonucleic acids with varying GC content. *Genome Research*, 6, 633-638.
18. Weiner, M. P., Costa, G. L., Schoettlin, W., Cline, J., Mathur, E. and Bauer, J. C. (1994) Site-directed mutagenesis of double-stranded DNA by the polymerase chain reaction. *Gene*, 151, 119-123.
19. Dower, W. J., Miller, J. F. and Ragsdale, W. (1988) High efficiency transformation of *E. coli* by high voltage electroporation. *Nucleic Acids Research*, 16, 6127-6145.
20. Studier, W. F., Rosenberg, A. H., Dunn, J. J. and Dubendorff, J. W. (1990) Use of T7 RNA polymerase to direct expression of cloned genes. *Methods in Enzymology*, 185, 60-89.
21. Bevis, B. J. and Glick, B. S. (2002) Rapidly maturing variants of the Discosoma red fluorescent protein (DsRed). *Nature Biotechnology*, 20, 83-87.
22. Barnes, W. M. and Frawley, E. 2003. Streamlined Gene Assembly PCR. p. 475-481. In Dieffenbach, C. W. and Dveksler, G. S. (Eds.), PCR Primer, 2d ed. Cold Spring Harbor Press, NY.
23. Datsenko, K. A. and Wanner, B. L. (2000) One-step inactivation of chromosomal genes in *Escherichia coli* K-12 using PCR products. *Proc. Natl. Acad. Sci. U.S.A.*, 97, 6640-6645.
24. Hamilton, M. D., Nuara, A. A., Gammon, D. B., Buller, R. M. and Evans, D. H. (2007) Duplex strand joining reactions catalyzed by vaccinia virus DNA polymerase. *Nucleic Acids Research*, 35, 143-151.
25. Yu, M. and Masker, W. (2001) T7 Single Strand DNA Binding Protein but Not T7 Helicase Is Required for DNA Double Strand Break Repair. *Journal of Bacteriology*, 183, 1862-1869.
26. Kerr, C. and Sadowski, P. D. (1975) The involvement of genes 3, 4, 5 and 6 in genetic recombination in bacteriophage T7. *Virology*, 65, 281-285.
27. Sadowski, P. D. and Vetter, D. (1975) Genetic recombination of bacteriophage T7 DNA in vitro. *Proc. Natl. Acad. Sci*, 73, 692-696.
28. Lee, D. and Sadowski, P. D. (1983) In vitro recombination of bacteriophage T7 DNA detected by a direct physical assay. *J. Virology*, 48, 647-653.
29. Barnes, W. M. (1997) *Thermus aquaticus* DNA polymerase lacking the N-terminal 235 amino acids of taq DNA polymerase. U.S. Pat. No. 5,616,494.

What is claimed is:

1. A method of generating a recombinant DNA molecule comprising:
forming a reaction mixture comprising a T7 5' exonuclease, a thermostable polymerase, a plurality of dNTPs selected from the group consisting of dATP, dTTP, dCTP, and dGTP, a first DNA molecule; and a second DNA molecule;
contacting a T7 5' exonuclease and at least two DNA molecules comprising a first linear double stranded DNA molecule and a second linear double stranded DNA molecule at a first incubation temperature of between 5° C. and 0° C. and for a first incubation time sufficient to create a 3' overhang on the first DNA molecule and the second DNA molecule, wherein
the first DNA molecule and the second DNA molecule are substantially homologous at terminal ends for at least about 15 up to about 50 bases;
inactivating the T7 5' exonuclease at a second incubation temperature for a second incubation time sufficient to inactivate the T7 5' exonuclease without substantially denaturing the at least two DNA molecules;
annealing homologous ends of the first DNA molecule and the second DNA molecule at a third incubation temperature for a third incubation time sufficient to form an annealed complex; and
contacting the annealed complex, at least one thermostable polymerase, and a plurality of dNTPs during the third incubation time to allow extension of a 3' end of the first DNA molecule or the second DNA molecule, thereby filling a gap corresponding to exonuclease removal, to form a substantially non-gapped annealed complex;
wherein the substantially non-gapped annealed complex is capable of transformation into a host cell without further in vitro processing.

2. The method of claim 1, wherein the first incubation temperature is 0° C.

3. The method of claim 1, wherein the first incubation time is about 5 minutes to about 15 minutes.

4. The method of claim 3, wherein the first incubation time is about 15 minutes.

5. The method of claim 1, wherein the second incubation temperature is about 75° C.

6. The method of claim 1, wherein the second incubation time is about 15 minutes.

7. The method of claim 1, wherein the third incubation temperature is about 44° C. to about 55° C.

8. The method of claim 7, wherein the third incubation temperature is about 52° C.

9. The method of claim 1, wherein the third incubation time is about 10 minutes.

10. The method of claim 1, wherein the first DNA molecule is a target DNA molecule and the second DNA molecule is a linearized vector.

11. The method of claim 10 wherein the vector is selected from the group consisting of: a bacterial vector, a viral vector, a yeast vector, a plant vector, and an animal cell vector.

12. The method of claim 1, wherein the non-gapped annealed complex is a linear non-gapped annealed complex.

13. The method of claim 1, wherein the non-gapped annealed complex is a circular non-gapped annealed complex.

14. The method of claim 1, wherein the first DNA molecule and the second DNA molecule are substantially homologous at terminal ends for at least about 18 up to about 40 bases.

15. The method of claim 14, wherein the first DNA molecule and the second DNA molecule are substantially homologous at terminal ends for at least about 22 up to about 33 bases.

16. The method of claim 15, wherein the first DNA molecule and the second DNA molecule are substantially homologous at terminal ends for at least about 24 up to about 36 bases.

17. The method of claim 1, wherein the annealed complex comprises about 3 to about 5 linked DNA molecules.

18. The method of claim 1 wherein the T7 exonuclease is present at about 0.7 units per 20 µl reaction volume.

19. The method of claim 1, wherein contacting the T7 5' exonuclease and the at least two DNA molecules occurs in a reaction mixture comprising about 1 to about 10 mM DTT.

20. The method of claim 19 wherein contacting the T7 5' exonuclease and the at least two DNA molecules occurs in a reaction mixture comprising about 10 mM of substantially non-oxidized DTT.

21. The method of claim 1, wherein contacting the T7 5' exonuclease and the at least two DNA molecules occurs in a reaction mixture comprising about 100 µg/ml BSA.

22. The method of claim 1, wherein the at least one thermostable polymerase is selected from the group consisting of a Taq polymerase and a Klentaq polymerase.

23. The method of claim 1 wherein contacting the annealed complex, at least one thermostable polymerase, and the plurality of dNTPs comprises:
contacting the annealed complex, the plurality of dNTPs, and a polymerase mixture comprising (i) an Archeal polymerase and (ii) one or more of a Taq polymerase and a Klentaq polymerase.

24. The method of claim 1, wherein the at least one thermostable polymerase is present at about 0.25 units per 20 µl reaction volume.

25. The method of claim 1, further comprising:
transforming or transfecting a host cell with the substantially non-gapped annealed complex.

26. The method of claim 25 wherein the host cell is transformed or transfected with the substantially non-gapped annealed complex directly from an annealing and extending reaction mixture without further in vitro processing.

27. The method of claim 25, wherein the yield of transformants or transfectants is greater than about 100 transfected or transformed host cells per 10 ng of the first DNA molecule, wherein the first DNA molecule is a target DNA molecule.

28. The method of claim 25, wherein the yield of transformants or transfectants is at least about 1,000 to about 3,000 clones per ng of first DNA molecule, wherein the first DNA molecule is a target DNA molecule.

29. The method of claim 26, wherein the host cell is an *E. coli*.

30. The method of claim 1, further comprising:
amplifying the first DNA molecule in a polymerase chain reaction (PCR); and
removing or de-activating substantially all primers used in the PCR of the first DNA molecule.

31. The method of claim 30 wherein the PCR comprises one or more polymerases selected from the group consisting of Vent, Deep Vent, Pfu, Klentaq1, KlentagLA, TaqLA, Taq, or KOD, or mixtures thereof.

32. The method of claim 1, wherein the first DNA molecule is at a concentration less than about 0.5 ng per ul of a reaction mixture; less than about 0.4 ng per ul of a reaction mixture; or less than about 0.3 ng per ul of a reaction mixture.

33. The method of claim 1, further comprising:
forming a reaction mixture comprising the 5' exonuclease; the thermostable polymerase; a plurality of dNTPs selected from the group consisting of dATP, dTTP, dCTP, and dGTP; the first DNA molecule; and the second DNA molecule;
wherein
no further additions are made to the reaction mixture and the reaction mixture is only manipulated thereafter as to temperature; and
the substantially non-gapped annealed complex formed from the reaction mixture is capable of transformation into a host cell without further in vitro processing.

34. The method of claim 33, wherein the first incubation temperature is 0° C.; the second incubation temperature is about 75° C.; and the third incubation temperature is about 44° C. to about 55° C.

35. The method of claim 34, wherein the first incubation time is about 5 minutes to about 15 minutes; the second incubation time is about 15 minutes; and the third incubation time is about 10 minutes.

36. The method of claim 33, wherein the reaction mixture further comprises DTT.

37. The method of claim 33, wherein the reaction mixture further comprises BSA.

38. The method of claim 1, not including use of one or more of a restriction enzyme; a restriction site sequence; a joining enzyme; a topoisomerase; or a recombinase.

39. The method of claim 38 not including use of any of a restriction enzyme; a restriction site sequence; a joining enzyme; a topoisomerase; or a recombinase.

* * * * *

UNITED STATES PATENT AND TRADEMARK OFFICE
CERTIFICATE OF CORRECTION

PATENT NO.        : 9,234,226 B2
APPLICATION NO.   : 13/124369
DATED             : January 12, 2016
INVENTOR(S)       : Wayne M. Barnes It is certified that error appears in the above-identified patent and that said Letters Patent is hereby corrected as shown below:

On the Title Page of the patent

Related U.S. Application Data (delete):
"(62) Division of application No. 61/196,060 filed on Oct. 14, 2008."

Related U.S. Application Data (insert):
--(62) Provisional application No. 61/196,060 filed on Oct. 14, 2008.--

Signed and Sealed this
Nineteenth Day of April, 2016

Michelle K. Lee
*Director of the United States Patent and Trademark Office*